United States Patent
Huang et al.

(10) Patent No.: US 8,426,623 B2
(45) Date of Patent: Apr. 23, 2013

(54) SURFACE MODIFIED NANOPARTICLE AND PREPARATION METHOD THEREOF

(75) Inventors: Yuh-Jeen Huang, Hsinchu (TW); Kuan-Yi Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 339 days.

(21) Appl. No.: 12/871,195

(22) Filed: Aug. 30, 2010

(65) Prior Publication Data
US 2011/0295030 A1    Dec. 1, 2011

(30) Foreign Application Priority Data

May 28, 2010 (TW) ................ 99117168 A (51) Int. Cl.
| C07F 7/00 | (2006.01) |
| C07F 15/00 | (2006.01) |
| C07F 1/00 | (2006.01) |
| C07F 3/00 | (2006.01) |

(52) U.S. Cl.
USPC ............... 556/54; 556/81; 556/113; 556/130; 556/138; 556/181; 977/773; 977/882; 562/478

(58) Field of Classification Search ............ 556/54, 556/81, 113, 130, 138, 181; 977/773, 882; 562/478; 55/54, 81
See application file for complete search history.

(56) References Cited

PUBLICATIONS

Chen, et al., "The effect of functional CuO nanoparticles on the decrease of cell cytoxicity caused by CuO nanoparticles", Department of Biomedical Engineering and Environmental Sciences, National Tsing-Hua University, Hsinchu 30013, Taiwan, ROC., May 26, 2010.
Karlsson, et al., Copper Oxide Nanoparticles Are Highly Toxic: A Comparison between Metal Oxide Nanoparticles and Carbon Nanotubes, Chem. Res. Toxicol, 2008, 21, pp. 1726-1732.
Chen, et al., The effect of functional CuO nanoparticles on the decrease of cell cytoxicity caused by CuO nanoparticles, Department of Biomedical Engineering and Environmental Sciences, National Tsing-Hua University, Hsinchu, 30013, Taiwan, ROC, (2009).

*Primary Examiner* — Porfirio Nazario Gonzalez
(74) *Attorney, Agent, or Firm* — Muncy, Geissler, Olds & Lowe, PLLC (57) ABSTRACT

A surface modified nanoparticle includes a nanoparticle and a phenol compound used for modifying the nanoparticle. The phenol compound has a formula of (a) or (b), wherein n=1~9, X is selected from the group consisted of $NH_2$, OH, $PH_4$, COOH and SH, R1 is selected from the group consisted of C1-C5 alkyl group, aryl group, alkenyl group, alkynyl group, alkylamino group and alkoxy group. Each carbon atom of the phenol group may be independently substituted or non-substituted. The substituent of the carbon atom of the phenol may be selected from the group consisted of halogen, C1-C5 alkyl group, cyano (CN), trifluoromethyl ($CF_3$), alkylamino group, amino and alkoxy group. The present invention may be used for anti-oxidant and/or decreasing the toxicity of the nanoparticle. A preparation method of surface modified nanoparticle is also herein provided.

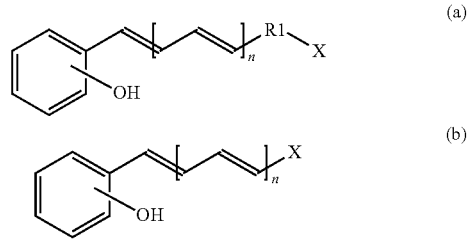

18 Claims, 5 Drawing Sheets

SURFACE MODIFIED NANOPARTICLE AND PREPARATION METHOD THEREOF

BACKGROUND OF THE INVENTION

1. Field of the Invention

The present invention relates to a surface modified nanoparticle and preparation method thereof, more particularly to a nanoparticle surface modified with a phenol compound having dienoic bonds and preparation method thereof.

2. Description of the Prior Art

With advance of nanotechnology development, there have been numerous and versatile nanotechnology products in our daily life. Nanomaterials surface modified with specific molecules have been broadly applied in many aspects. For example, nanoparticles made of magnetic iron oxide, gold, CdSe quantum dot may be used as vehicles and surface modified with special functional molecules, e.g. organic compounds, fatty acids, DNA, so as to be applied in drug delivery, environmental analysis and other particular purposes.

When processed to nanometer-size, conventional materials may be varied in their physical, chemical properties and biocompatibility. Particles or structure material sized between 1 and 100 nanometers, i.e. nanoparticles, may be uptaken into living organisms via breath, diet, blood vessel injection, skin contact and so on. For example, nanoparticles suspended in air may be inhaled into lungs of living organisms or nanoparticles existing in contaminated water or food may enter into gastrointestinal tracts. In addition, nanometer-sized medicine may enter living organisms via intravenous injection, or applying external medicine or cosmetics containing nanoparticles on skin.

Nanoparticles, especially non-organic nanomaterial, are characterized in quick absorption, slow excrement and therefore long retention period. The nanoparticles that retain in the living organism might result in tissue inflammation, necrosis and fibrosis in some cases, and might cause mitochondria deformation and cell death in the other cases.

The toxicity of nanoparticles may depend on their own material properties, including biocompatibility, physical property, chemical property, mechanical property, radius, shape and so on. In addition, the solubility and concentration of nanoparticles that enter tissues and cells also contribute to the toxicity.

It is currently thought that the primary mechanisms for nanoparticle toxicity are cell-generated peroxide radicals. Reactive oxygen species (ROS), including $O_2^-$, $H_2O_2$, —OH and so on, are characterized in free radicals having unpaired electrons and therefore are highly active and might attack important molecules, e.g. proteins, nucleic acids and fatty acid, resulted in cellular oxidative damage and further aging or disease.

It would be very difficult to keep alert since one can not be aware of being exposed in environment containing nanoparticles. Although nanoparticles have been broadly applied, we still haven't understood the mechanisms for absorption, distribution, metabolism, excretion and toxicity after nanoparticles are uptaken into human. Therefore, it is now an urgent and important mission to provide safe nanoparticles for human.

SUMMARY OF THE INVENTION

The present invention is directed to a surface modified nanoparticle used for antioxidants and/or detoxifying the nanoparticle.

According to one embodiment, a surface modified nanoparticle includes a nanoparticle and a phenol compound used for modifying the nanoparticle. The phenol compound has a formula of (a) or (b), wherein n=1~9, X is selected from the group consisting of $NH_2$, OH, $PH_4$, COOH and SH, R1 is selected from the group consisting of C1-C5 alkyl group, aryl group, alkenyl group, alkynyl group, alkylamino group and alkoxy group. Each carbon atom of the phenol group may be independently substituted or non-substituted. The substituent of the carbon atom of the phenol may be selected from the group consisting of halogen, C1-5 alkyl group, cyano (CN), trifluoromethyl ($CF_3$), alkylamino group, amino and alkoxy group.

According to another embodiment, a method for surface modifying a nanoparticle, includes providing a nanoparticle; providing a phenol compound having a chemical formula represented by formula (a) or (b), wherein n=1~9, X is selected from the group consisting of $NH_2$, OH, $PH_4$, COOH and SH, R1 is selected from the group consisting of C1-C5 alkyl group, aryl group, alkenyl group, alkynyl group, alkylamino group and alkoxy group; and each carbon atom of the phenol group is independently substituted or non-substituted, and the substituent of the carbon atom of the phenol is selected from the group consisting of halogen, C1-C5 alkyl group, cyano (CN), trifluoromethyl ($CF_3$), alkylamino group, amino and alkoxy group; and providing the phenol compound and the nanoparticle in a solution and undergoing a reaction to get a surface modified nanoparticle.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein.

DESCRIPTION OF THE PREFERRED EMBODIMENT

The present invention is directed to a nanoparticle modified with a phenol compound with dienoic bonds and used for antioxidants and/or detoxifying the nanoparticle.

Selecting Nanoparticles

There are no limits on the physical parameters of a nanoparticle component of the present invention. However, the physical parameters of a nanoparticle can be optimized with the desired effect governing the choice of size, shape and material.

In one embodiment, the nanoparticles of the present invention may be made of metal and the oxide thereof, including without limitation to Au, Ag, Fe, Co, Ni, Ti, Zn, Sn, Cu, Al or the oxides of above-mentioned metals.

Due to low toxicity and anti-oxidizing capability, gold and silver nanoparticles may be chosen and used in clinical medicine when considering candidate nanoparticles for drug delivery vehicle.

In addition, magnetic nanoparticles, including Fe, Co, Ni and the oxides thereof, have advantages in being detectable and tractable and may also be candidate nanoparticles for delivery vehicle.

The present invention may also be directed to other surface-modified metalloid, including without limitation to CdSe, $SiO_2$ and diamond.

In addition, the present invention may be applied for surface-modifying and detoxifying toxic nanoparticles. For example, Karlsson et al (Chem. Res. Toxicol. 21, 1726-1732 (2008)) studied the in vitro toxicity of metal oxide nanoparticles and found that CuO nanoparticle is the most toxic nanoparticle in the study and has great cytotoxicity and causes DNA damages. Also, ZnO nanoparticle would influence the cell viability and cause DNA damage; and $TiO_2$ nanoparticle would cause DNA damage only.

Nanoparticles usually refer to particles or structure material in 1~100 nm; however, the nanoparticles referred in the present invention may have any other average particle size based on some specific usage. The average particle size is referred to the size of nanoparticles, which may include the phenol compounds of the present invention, measured by conventional measuring methods. The average particle size may relate to the number, shape and size of at least one nanocrystal present and can be variable. Generally speaking, the average particle size is less than 100 nm.

However, the present invention may also be applied in detoxifying nanoparticles, which may be in a form of aggregates having average particle size larger than 1 μm or between 100 nm and 100 μm.

Phenol Compounds

The phenol compounds of the present invention include double conjugate systems, i.e. the benzene structure of phenol and dienoic bond, resulted in good electron resonance structure. Therefore, the phenol compounds of the present invention may be used for free radical scavenging, such as $O_2^-$, $H_2O_2$, —OH and so on.

The phenol compound of the present invention may have a chemical formula represented by formula (a) or (b), wherein n=1~9.

(a)

(b)

X is used for modifying the nanoparticles and may be selected from the group consisting of $NH_2$, OH, $PH_4$, COOH and SH. Optionally, R1 may be present between the conjugated double dienolic bound and functional group X. R1 is selected from the group consisting of C1-5 alkylene group and aryl group. Each carbon atom of the phenol group is independently substituted or non-substituted, and the substituent of the carbon atom of the phenol is selected from the group consisting of halogen, C1-C5 alkyl group, cyano (CN), trifluoromethyl ($CF_3$), alkylamino group, amino and alkoxy group.

In one preferred embodiment, the phenol compounds of the present invention have a chemical formula represented by formula (c) or (d).

(c)

(d)

In other words, the R1 in formula (a) or (b) may be connected to the conjugated dienolic bond with ester bond or peptide bond. R2 is selected from the group consisting of C1-C5 alkylene group, and aryl group. Each carbon atom of the phenol group is independently substituted or non-substituted, and the substituent of the carbon atom of the phenol is selected from the group consisting of halogen, C1-C5 alkyl group, cyano (CN), trifluoromethyl ($CF_3$), alkylamino group, amino and alkoxy group.

Nanoparticle Modification

Nanoparticle modification mentioned in the present invention refers to binding of compound to the nanoparticles so as to increase and/or adjust the physical properties, chemical properties and uses of nanoparticles.

As fore-mentioned, the phenol compound may include a functional group for modifying nanoparticles, for example without limitation to $NH_2$, OH, $PH_4$, COOH and SH.

In one embodiment, the phenol compound may include SH functional group so as to bind to gold, silver nanoparticles.

In one embodiment, the phenol compound having a conjugated carboxyl group is adopted for modifying the nanoparticle, wherein the solution pH is adjusted so as to increase the binding of the phenol compound to the nanoparticle without damaging the hydroxyl group in the phenol compound. To be specific, the conjugated carboxyl group has pKa<4.2, and the hydroxyl group of the phenol compound has pKa≈10. Therefore, the pH value of the solution may be adjusted to lower than the pKa value of the conjugated carboxyl group (≈4.2) so as to prevent from damaging the hydroxyl group of the phenol compound.

The following descriptions of specific embodiments of the present invention have been presented for purposes of illustrations and description, and they are not intended to be exclusive or to limit the present invention to the precise forms disclosed, and obviously many modifications and variations are possible in light of the above teaching. It is intended that the scope of the invention be defined by the Claims appended hereto and their equivalents.

Phenol Compound

One preferred example compound of the present invention is represented with (2E,4E)-5-(4-hydroxyphenyl)penta-2,4-dienoic acid (herein abbreviated HPPDA) having a chemical formula listed below:

Structure data: $^1$H NMR (400 MHZ, d-acetone): δ (ppm) 5.92 (s, $H_c$, 1H), 5.98 (s, $H_b$, 1H), 6.85 (s, $H_d$, 1H), 6.88 (s, $H_a$, 1H), 6.92-7.45 (dd, $H_e$, $H_f$, 4H)

Anti-Oxidative Activity of Phenol Compound $H_2O_2$ was the tested ROS in testing anti-oxidative activity of HPPDA. There are 3 sets in this experiment, including $H_2O_2$, HPPDA/$H_2O_2$ and ascorbic acid/$H_2O_2$, where HPPDA/$H_2O_2$=1, ascorbic acid/$H_2O_2$=1, and HPPDA, ascorbic were respectively reacted with $H_2O_2$ before $H_2O_2$ was measured. The control is represented with $H_2O_2$ without undergoing any reaction.

Figure 1:
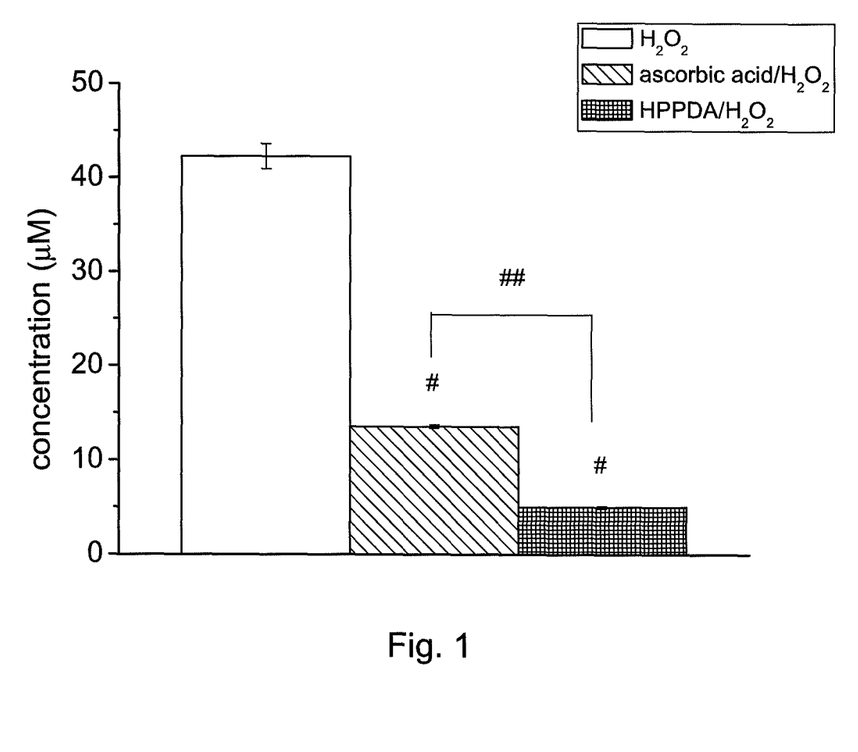
FIGS. 1 to 5 are diagrams illustrating the experiment outcome according to one embodiment of the present invention.

Referring to FIG. 1, as the comparison result with control has shown, the concentration of $H_2O_2$ was lowered after reacted with ascorbic acid and HPPDA (# for significant difference, p<0.01). Particularly, $H_2O_2$ concentration was lowered by ascorbic acid with 30 μM and lowered by HPPDA with 40 μM; this means better $H_2O_2$ absorption by HPPDA than ascorbic acid.

Preparation of Surface-Modified Nanoparticles

For nanoparticle surface modification, the nanoparticles was dissolved with pure water and adjusted to pH=3. The solution is added with HPPDA for over night reaction, and then filtered, washed with water, dried to obtain solid as modified nanoparticles.

Toxicity Test

Toxicity test includes testing of cell viability, inflammation and anti-oxidation. The target cell is A549 cell line (Human lung adenocarcinoma epithelial cell line) and the exposed time was 24 hours.

(1) Cell Viability

Figure 2:
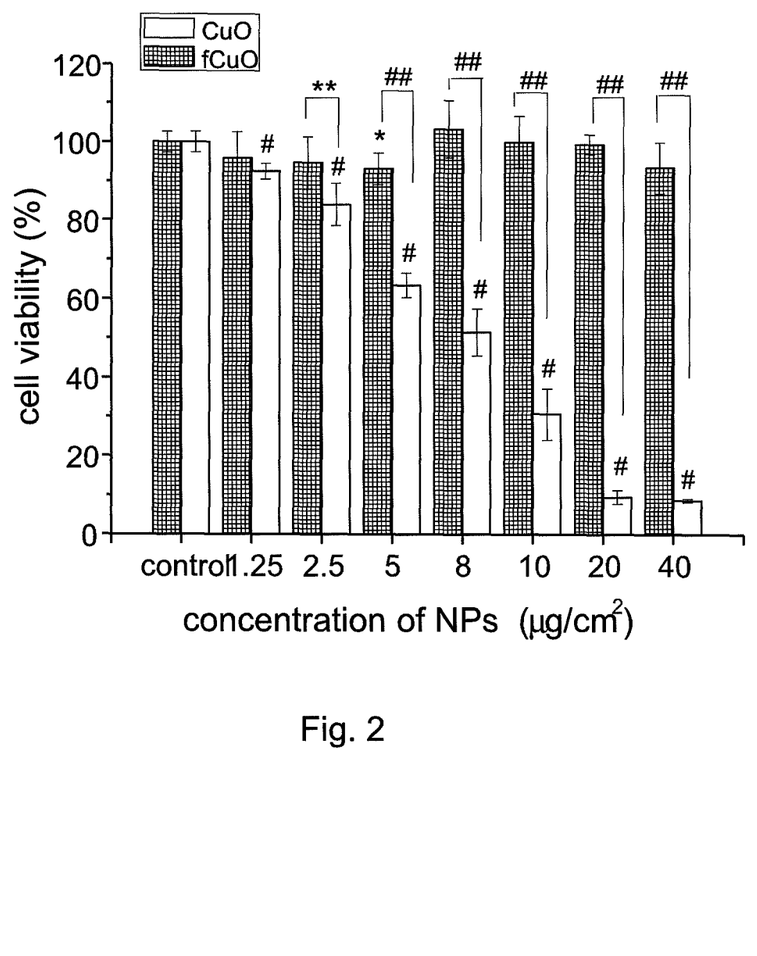

FIG. 2 illustrates the cell toxicity test of CuO and fCuO (HPPDA modified CuO) represented by cell viability after exposed to CuO and fCuO for 24 hours. There is significant difference for CuO and fCuO in comparison to the control, where # for p<0.01 and * for p<0.05. In addition, there is significant difference between CuO and fCuO at 5 μg/cm$^2$, where ## for p<0.01 and ** for p<0.05. As illustrated, the cell viability decreases as CuO concentration increases; particularly, the cell viability is less than 10% as the nanoparticle concentration is over 20 μg/cm$^2$. However, in the presence of fCuO (HPPDA-modified CuO nanoparticle), the cell viability may be maintained at 93~100%. Therefore, CuO is highly cytotoxic and HPPDA modification would significantly alleviate that. The data is from a 4-repeat experiment, and the control is the cells unexposed to the nanoparticles.

(2) IL-8 Secretion

Figure 3:
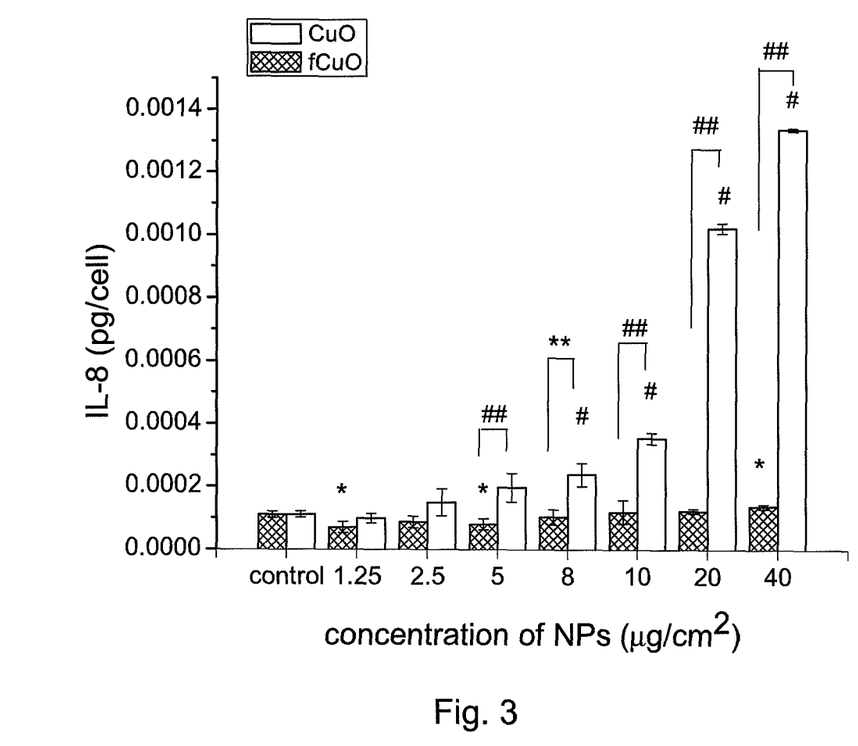

FIG. 3 illustrates the cell inflammation test of CuO and fCuo (HPPDA modified CuO) represented by IL-8 (Interleukin-8) secretion after A549 cells were exposed to CuO and fCuO for 24 hours. The data was from a 4-repeat experiment, and the control is the cells unexposed to the nanoparticles. There is significant difference for CuO and fCuO in comparison to the control, where # for p<0.01 and * for p<0.05. In addition, there is significant difference between CuO and fCuO at 5 μg/cm$^2$, where ## for p<0.01 and ** for p<0.05.

As illustrated, the IL-8 secretion increases as CuO concentration increases; particularly, the elicitation tendency becomes even more significant as the nanoparticle concentration is over 10 μg/cm$^2$. However, in the presence of fCuO (HPPDA-modified CuO nanoparticle), the secreted amount of IL-8 does not go up in comparison of control, even as the concentration of nanoparticles increases. Therefore, CuO may elicit the cellular inflammation, which may be significantly alleviated by HPPDA modification.

(3) Anti-ROS

Figure 4:
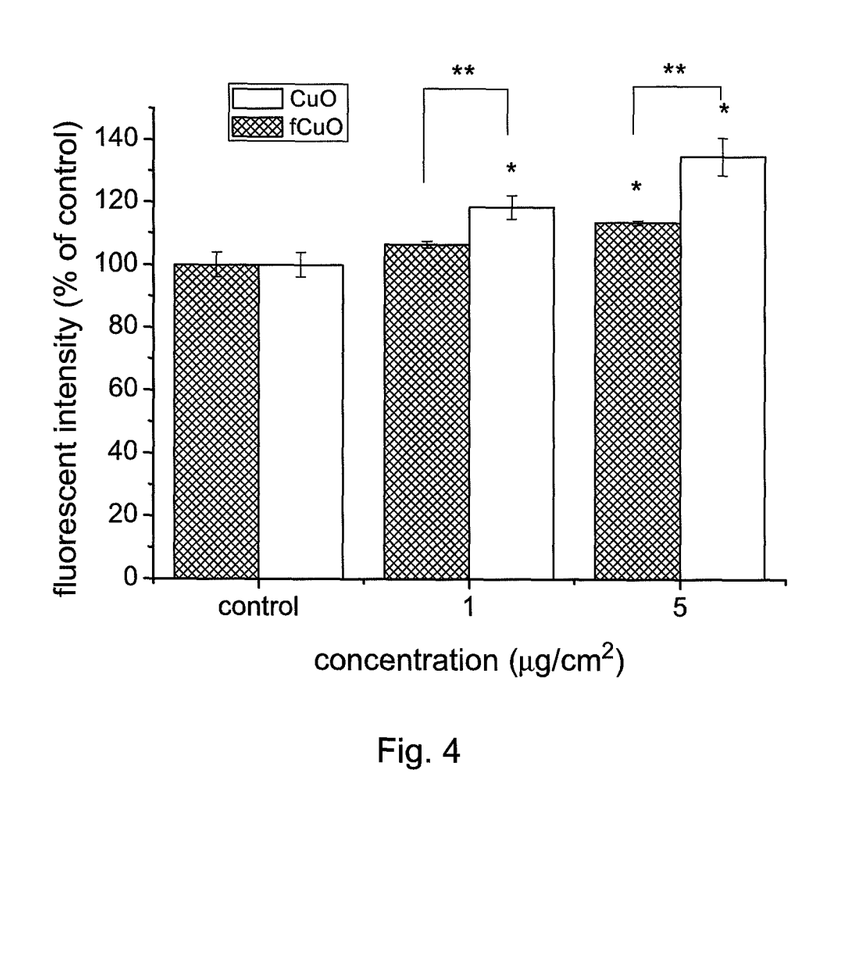

FIG. 4 illustrates the anti-ROS test of CuO and fCuO (HPPDA modified CuO) represented by DCFH-DA-titrated intracellular ROS generation in A549 after exposed to CuO and fCuO for 24 hours. The data was from a 2-repeat experiment, and the control was the cells unexposed to the nanoparticles, where * represents significant difference between the experiment result and the control (p<0.05), and ** represents significant difference between fCuO and CuO (p<0.05). The X axis represents the fluorescence intensity of the control group (100%), and the fluorescence intensity of the experimental group was compared to the control group. The Y axis represents the exposed nanoparticle concentration. As illustrated, the elicited ROS increases as CuO concentration increases; however, the intracellular ROS generation would be alleviated after HPPDA modification.

(4) Anti-DNA Oxidation

Figure 5:
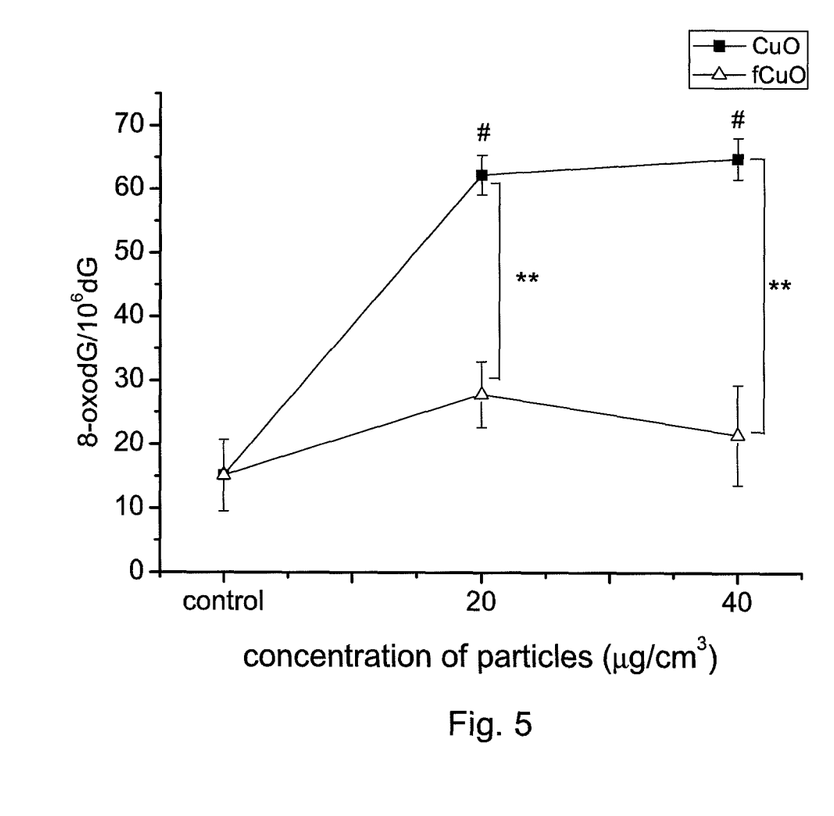

FIG. 5 illustrates the anti-ROS test of CuO and fCuO represented by levels of 8-oxodG (8-Oxo-2'-deoxyguanosine) in dG standard solution after A549 cells exposed to CuO and fCuO for 3 hours. The data was from a 2-repeat experiment, and the control was the cells unexposed to the nanoparticles, where # represents significant difference between CuO group and the control (p<0.01), and ** represents significant difference between fCuO and CuO (p<0.05). The data illustrates that the 8-oxodG may be elicited with CuO; however, the oxidative DNA damage would be alleviated after HPPDA modification.

To sum up, the surface-modified nanoparticle of the present invention is capable of lowering cytotoxicity and being anti-oxidative and may be useful for application in environmental protection, medicine, materials and cosmetics. For example, the present invention may be used as a nanoparticle delivery vehicle for cleaning up human blood vessels and damages caused by intracellular reactive oxygen species. In addition, the method for surface modifying the nanoparticle may be used as the post-processing of waste nanomaterials so as to lessen the impact to the environment and living organism.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:
1. A surface-modified nanoparticle, comprising:
a nanoparticle; and
a phenol compound modifying the nanoparticle and having a chemical formula represented by formula (a)-(d), wherein
n=1~9;
X is selected from the group consisting of $NH_2$, OH, $PH_4$, COOH and SH;
each of R1 and R2 is selected from the group consisting of C1-C5 alkylene group and aryl group; and
each carbon atom of the phenol group is independently substituted or non-substituted, and the substituent of the carbon atom of the phenol is selected from the group consisting of halogen, C1-C5 alkyl group, cyano (CN), trifluoromethyl ($CF_3$), alkylamino group, amino and alkoxy group.

2. The surface-modified nanoparticle as claimed in claim 1, wherein the nanoparticle is made of metal or the oxide thereof.

3. The surface-modified nanoparticle as claimed in claim 2, wherein the nanoparticle is made of gold or silver.

4. The surface-modified nanoparticle as claimed in claim 3, wherein the phenol compound has a chemical formula listed below,

5. The surface-modified nanoparticle as claimed in claim 2, wherein the nanoparticle is made of the group consisting of iron, cobalt, nickel, titanium, zinc, tin, copper, aluminum and the oxides of above-mentioned metals.

6. The surface-modified nanoparticle as claimed in claim 1, wherein the nanoparticle is made of the group consisting of CdSe, $SiO_2$ and diamond.

7. The surface-modified nanoparticle as claimed in claim 1, wherein the phenol compound has a chemical formula listed below, 8. A method for surface modifying a nanoparticle, comprising:
providing a nanoparticle;
providing a phenol compound having a chemical formula represented by formula (a)-(d), wherein
n=1~9;
X is selected from the group consisting of $NH_2$, OH, $PH_4$, COOH and SH;
each of R1 and R2 is selected from the group consisting of C1-C5 alkylene group and aryl group; and
each carbon atom of the phenol group is independently substituted or non-substituted, and the substituent of the carbon atom of the phenol is selected from the group consisting of halogen, C1-C5 alkyl group, cyano (CN), trifluoromethyl ($CF_3$), alkylamino group, amino and alkoxy group; and
providing the phenol compound and the nanoparticle in a solution and undergoing a reaction to get a surface modified nanoparticle, (b)

(c)

(d)

9. The method as claimed in claim 8, wherein the nanoparticle is made of metal or the oxide thereof.

10. The method as claimed in claim 9, wherein the nanoparticle is made of gold or silver.

11. The method as claimed in claim 10, wherein the phenol compound has a chemical formula listed below, 12. The method as claimed in claim 9, wherein the nanoparticle is made of the group consisting of iron, cobalt, nickel, titanium, zinc, tin, copper, aluminum and the oxides of above-mentioned metals.

13. The method as claimed in claim 8, wherein the nanoparticle is made of the group consisting of CdSe, $SiO_2$ and diamond.

14. The method as claimed in claim 8, wherein the phenol compound has a chemical formula listed below, 15. The method as claimed in claim 14, wherein the pH value of the solution is less than the pKa value of the COON group of the phenol compound.

16. The method as claimed in claim 8, wherein the nanoparticle has a diameter less than 100 nm.

17. The method as claimed in claim 8, wherein the nanoparticle has a diameter between 100 nm and 100 μm.

18. The method as claimed in claim 8, being used for detoxifying the nanoparticle.

* * * * *